United States Patent [19]

Fišnerová et al.

[11] Patent Number: 4,973,691

[45] Date of Patent: Nov. 27, 1990

[54] ETHERIC DERIVATIVE OF 4(3H)-QUINAZOLINONE AND A PROCESS FOR PREPARATION THEREOF

[75] Inventors: Ludmila Fišnerová, Zvonková; Bohumila Brůnová, Ostrovského; Eva Maturová, Zvonková; Jaroslava Grimová, Praha, all of Czechoslovakia

[73] Assignee: Spojene Podniky Prozdravotnickou Vyrobu (SPOFA), Czechoslovakia

[21] Appl. No.: 430,293

[22] Filed: Nov. 1, 1989

[30] Foreign Application Priority Data

Nov. 1, 1988 [CS] Czechoslovakia ............... 7195-88

[51] Int. Cl.$^5$ ............................................. C07D 239/74
[52] U.S. Cl. ..................................... 544/283; 568/642
[58] Field of Search ......................................... 544/283

[56] References Cited

U.S. PATENT DOCUMENTS 3,454,574  7/1969  Keck et al. .................... 544/283

OTHER PUBLICATIONS

D. B. Reisner et al. "2,3—Dihydro—9H—Isoxazolo[3,2—b]quinzolin—9—ones and 3,4—Dihydro—(1,2)—oxazino[3,2—b]quinazolin—10(2H)—ones," Drug Res. 27(I), No. 4, pp. 766-770 (1977).

*Primary Examiner*—Richard L. Raymond
*Assistant Examiner*—James H. Turnipseed
*Attorney, Agent, or Firm*—Leydig, Voit & Mayer

[57] ABSTRACT

An etheric derivative of 4(3H)-quinazolinone which is a fluorinated 3-[2-(4-biphenylyloxy)ethyl]-4(3H)-quinazolinone, produced by reacting said 4(3H)-quinazolinone with the corresponding fluorinated 4-(2-chloroethoxy)biphenyl, and its acid addition salts, especially the hydrochloride. This compound possesses substantially higher analgesic activity and lower acute toxicity than aminophenazone, ibuprofen, acetylosalicyclic acid and paracetamol.

2 Claims, No Drawings

ETHERIC DERIVATIVE OF 4(3H)-QUINAZOLINONE AND A PROCESS FOR PREPARATION THEREOF

FIELD OF THE INVENTION

This invention generally relates to novel etheric derivatives of 4(3H)-quinazolinone and processes for their preparation.

BACKGROUND OF THE INVENTION

Prior to the discovery of the present invention, various drugs have been used as analgesic agents. Examples of these agents include aminophenazone, phenacetin, and acetylosalicylic acid. However, these drugs often elicit certain undesired adverse side effects. For example, extensive investigations of aminophenazone in recent years, this analgesic currently being employed as a standard reference compound in pharmacological tests for analgesic activity, have shown it to have potentially cancerogenic properties. As a result, many countries have either prohibited or substantially restricted its use. Thus, a need exists for a safe, yet effective, analgesic drug.

SUMMARY OF THE INVENTION

The present invention is directed toward etheric derivatives of 4(3H)-quinazolinone having the formula:

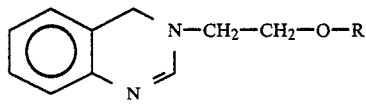

wherein R is selected from the group consisting of 4-biphenylyl, 2-biphenylyl, 2'4'-difluoro-4-biphenylyl, 2-naphyl, and 6-bromo-2-naphyl. More particularly, the invention contemplates an analgesic compound having the formula 3-[2-(2',4'-difluoro-4-biphenylyloxy)ethyl]-4(3H)-quinazolinone:

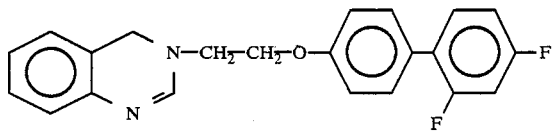

and its acid addition salts wherein said salts are produced from pharmaceutically acceptable organic or inorganic acids. The hydrochloride salt is the preferred form of the analgesic of the present invention.

The invention further relates to processes for the preparation of the aforesaid compounds and their acid addition salts. One of these processes generally comprises the reaction of 4(3H)-quinazolinone with an appropriate halogenated ether, e.g., 2',4'-difluoro-4-(2-chloroethoxy)biphenyl, this reaction yielding 3-[2-(2',4'-difluoro-4-biphenylyloxy)ethyl]-4-(3H)-quinazolinone. The reaction of these two components is advantageously conducted in the presence of sodium hydride in an inert organic solvent such as, e.g., dimethylformamide, and preferably at a temperature generally within the range of from about 90° C. to about 110° C. If desired, the resulting base may be converted by neutralization using an appropriate organic or inorganic acid, e.g., hydrochloric acid, into its respective addition salt. Although many different acids may be used to produce the acid addition salt, it is preferable that the acids be limited to those which will result in the formation of a pharmaceutically acceptable salt. For the purposes of this disclosure, these preferred acids will be referred to as pharmaceutically acceptable acids. As alluded to previously, the salts contemplated by the present invention are suitable for the preparation of medicinal dosages in the forms of, e.g. tablets or capsules, and for conducting biological assays.

The aforementioned novel compounds were tested for analgesic activity and exhibited remarkable activity and a substantially lower toxicity than aminophenazone (1-phenyl-2,3-dimethyl-4-dimethylamino-5-pyrazolone).

The etheric derivatives of quinazolinone contemplated by the present invention were selected as the pharmaceutical of choice from a number of related pharmaceuticals after subjecting said pharmaceuticals to a preliminary evaluation. During this evaluation, the preferred compound, especially its hydrochloride salt form, was found to possess remarkable properties which indicate that these compounds disclosed herein are useful as potent, yet safe, analgesic agents.

DETAILED DESCRIPTION OF THE INVENTION

The first starting compound, 4(3H)-quinazolinone, is a substance known to those skilled in the art. As such, it may be produced using any prior art method. A second starting material, 2',4'-difluoro-4-(2-chloroethoxy)-biphenyl:

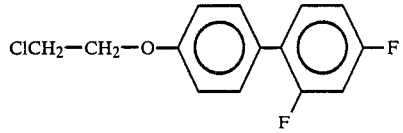

is a novel compound which may be prepared by reacting a substituted 4-hydroxybiphenyl derivative, e.g., 2',4'-difluoro-4-hydroxybiphenyl, with 2-chloroethylp-toluene-sulfonate (G. R. Clemo & W. H. Perkin, J. Chem. Soc. 642 (1922)).

The analgesic activity and acute (short-time) toxicity data, $ED_{50}$ and $LD_{50}$, respectively, both expressed in mg/kg p.o., is tabulated below for the aforesaid preferred etheric derivative and its hydrochloride salt. Further, aminophenazone, ibuprofen, 2-(4-isobutylphenyl)propionic acid, acetylosalicylic acid and paracetamo-4-hydroxyacetanilide are also included as reference compounds for comparison purposes.

| Compound | $ED_{50}$ | $LD_{50}$ |
|---|---|---|
| Preferred etheric derivative (3-[2-(2',4'-difluoro-4-biphenylyl)ethyl]-4(3H)-quinazolinone) (base) | 71 | 1000 |
| Preferred etheric derivative (hydrochloride salt) | 26 | 2000 |
| Aminophenazone | 104 | 800 |
| Ibuprofen (2-(4-isobutylphenyl) propionic acid) | 179 | 1258 |
| Acetylosalicylic acid | 190 | 1068 |
| Paracetamol | 285 | 1088 |

-continued

| Compound | ED$_{50}$ | LD$_{50}$ |
| --- | --- | --- |
| (4-hydroxyacetanilide) | | |

The novel etheric derivative and its salt also proved to be free of any signs of gastrotoxicity and cancerogenity.

EXAMPLES

The particulars of the instant process are illustrated by the subsequent Examples which are included for purposes of illustration only. These examples should not be considered as limiting the disclosure in any manner.

EXAMPLE 1

This example details the production of 2',4'-difluoro-4-(2-chloroethoxy)biphenyl. This procedure begins by combining a mixture of 58.5 g of 4-(2',4'-difluorophenyl)phenol, 13 g of sodium hydroxide, 26 ml of water and 66 g of 2-chloroethyl-p-toluenesulfonate and stirring said mixture for 2 hours at a temperature between about 95° C. and about 100° C. The resulting solution is then cooled to 20°-25° C. and is diluted with water. The final product is subsequently collected on a filter by crystallizing the product from the diluted solution using aqueous ethanol (2:1). The final product yield is 35 g (45% of theory), the final product having a melting point of 72°-74° C.

Using analogous preparative procedures, the following etheric derivatives of 4-(3N)-quinazolinone were also prepared: 3-[2-(4-biphenylyloxy)-ethyl]-4(3H)-quinazolinone, m.p. 185°-186° C.; 3-[2-(2-biphenylyloxy)-ethyl]-4(3H)-quinazolinone, m.p. 161°-162° C.; 3-[2-(2-naphtyloxy)-ethyl]-4(3H)-quinazolinone, m.p. 203°-204° C.; and 3-[2-(6-bromo-2-naphtyloxy)-ethyl]-4(3H)-quinazolinone, m.p. 246°-247° C.

EXAMPLE 2

The compound 2',4'-difluoro-4(2-chloroethoxy)-biphenyl is prepared by a process wherein to a solution of 15 g of sodium hydroxide in 30 ml of water there is added 68.2 g of 4-(2',4'-difluorophenyl)phenol and 106 g of 2-chloroethyl-p-toluene-sulfonate. The mixture is heated to about 95°-100° C. while stirring (at 96°-98° C. an exothermic reaction occurs) and maintained at this temperature for 5 hours. The resulting material is diluted with dichloromethane, washed with water, and evacuated until dry. The crude product is crystallized using isopropyl alcohol to yield 62 g (69% of theory) of the final product. If a further crop (9 g) of pure product can be obtained from the mother liquor, the total yield of the product is 80% of theory.

EXAMPLE 3

This example illustrates the production of 3-[2-(2',4'-difluoro-4-biphenylyloxy)ethyl]-4(3H)-quinazolinone wherein to a solution of 8.76 g of 4(3H)-quinazolinone in 120 ml of dimethylformamide there is gradually added 2 g of 80% sodium hydride having an initial temperature of 25° C. The mixture is then warmed to 100° C. while stirring maintained at this temperature for 15 minutes, and pre-cooled to 50° C. with 16.1 g of 2',4'-difluoro-4-(2-chloroethoxy)biphenyl being added in a single portion. The mixture is subsequently warmed again to a temperature of from about 98° C. to about 105° C. and maintained at this temperature for 2.5 hours. Upon cooling to 20°-25° C., the mixture is diluted with water and the crude product is separated, dried, and crystallized from ethyl acetate to yield 16.7 9 of the base. This base has a melting point of about 183°-184° C.

The aforementioned base may be converted to the hydrochloride by the following procedure. A solution of 16.7 g of the base prepared as above is added to 185 ml of chloroform. The resulting base-chloroform mixture is saturated with dry hydrogen chloride gas and then allowed to stand for 12 hours at a temperature of about 20°-22° C. while crystallization occurs. This process results in the production of 18 g of the desired hydrochloride.

What we claim is:

1. An etheric derivative of 4-(3H)-quinazolinone having the formula:

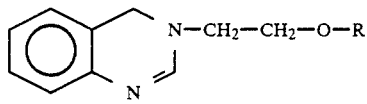

wherein R is a substituent selected from the group consisting of 4-biphenylyl, 2-biphenylyl, 2',4'-difluoro-4-biphenylyl, 2-naphyl, and 6-bromo-2-naphyl; and acid addition salts thereof wherein said salts are produced from pharmaceutically acceptable acids.

2. An etheric derivative of 4-(3H)-quinazolinone having the formula:

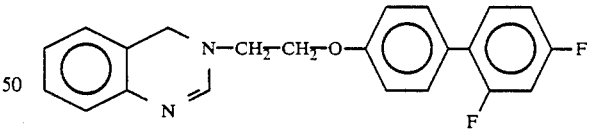

and acid addition salts thereof, wherein said salts are produced from pharmaceutically acceptable acids.

* * * * *